(12) United States Patent
Warner et al.

(10) Patent No.: US 7,927,298 B2
(45) Date of Patent: Apr. 19, 2011

(54) METHOD AND APPARATUS FOR INDUCING AND DETECTING ANKLE TORSION

(76) Inventors: Michael J. Warner, Johnstown, PA (US); James A. Mertz, Brick, NJ (US)

( * ) Notice: Subject to any disclaimer, the term of this patent is extended or adjusted under 35 U.S.C. 154(b) by 1450 days.

(21) Appl. No.: 11/159,696

(22) Filed: Jun. 23, 2005

(65) Prior Publication Data

US 2005/0288609 A1 Dec. 29, 2005

Related U.S. Application Data

(60) Provisional application No. 60/582,204, filed on Jun. 23, 2004.

(51) Int. Cl.
*A61F 5/00* (2006.01)
(52) U.S. Cl. .............................. 602/26; 602/32
(58) Field of Classification Search .............. 602/32–40; 482/131, 133; 128/882
See application file for complete search history.

(56) References Cited

U.S. PATENT DOCUMENTS

| | | | |
|---|---|---|---|
| 4,186,920 A * | 2/1980 | Fiore et al. | 482/79 |
| 4,483,532 A * | 11/1984 | Sparks | 482/79 |
| 4,595,198 A * | 6/1986 | Sparks | 482/119 |
| 4,733,859 A * | 3/1988 | Kock et al. | 482/79 |
| 4,824,104 A * | 4/1989 | Bloch | 482/6 |
| 4,979,737 A * | 12/1990 | Kock | 482/80 |
| 5,012,820 A * | 5/1991 | Meyer | 600/595 |
| 5,147,266 A * | 9/1992 | Ricard | 482/131 |
| 6,159,168 A * | 12/2000 | Warner et al. | 600/594 |

* cited by examiner

*Primary Examiner* — Michael A. Brown
(74) *Attorney, Agent, or Firm* — The Webb Law Firm

(57) ABSTRACT

A force applied to the foot of a patient causes the foot to rotate inwardly. After measuring the rotational displacement of the foot inwardly as the function of the applied force, the force is removed and the displacement of the foot is measured again. Next, a force is applied to the foot of the patient that causes the foot to rotate outwardly. After measuring the rotational displacement of the foot outwardly as a function of the applied force, the force is removed and the displacement of the foot is measured again. The displacements versus applied forces are plotted on a Cartesian coordinate system to produce a hysteresis curve. The data obtained and the hysteresis curve produced therefrom provides a quantitative measure of the motion quality and motion quantity of the foot and its corresponding ankle and is subject to detailed analytic and medical analysis.

24 Claims, 8 Drawing Sheets

METHOD AND APPARATUS FOR INDUCING AND DETECTING ANKLE TORSION

CROSS REFERENCE TO RELATED APPLICATION

This application claims the benefit of U.S. Provisional Patent Application No. 60/582,204, filed Jun. 23, 2004, and entitled "Method And Apparatus For Inducing And Detecting Ankle Torsion", the contents of which are incorporated herein by reference.

BACKGROUND OF THE INVENTION

1. Field of the Invention

The present invention relates to orthopedic and rheumatologic testing devices for body joints found in the extremities and digits and, more particularly, to an anatomic torsion monitor for detecting myofascial-musculoskeletal elasticity in a patient's ankle.

2. Description of Related Art

Treatment for orthopedic and rheumatologic problems of the extremities and digits is focused upon subjective complaints. Objective data, from imaging studies (x-ray, CAT scan, MRI) and blood tests (sedimentation rate, rheumatoid factor) may indicate the presence of a disease process (arthritis—bone surface changes, positive rheumatoid factor). Such objective data, however, does not measure the degree of function or dysfunction. Therefore, any treatment regimen can only be successful if the patient subjectively claims improvement. Such inefficiencies make orthopedic/rheumatologic problems very expensive for society to manage.

A common technique utilized by physicians to evaluate dysfunctions of the extremities and digits involves myofascial testing of joints. In this technique, the physician stabilizes the proximal part of the joint and applies a torsional twist to the distal portion of the joint. These techniques include indirect and direct approaches. With the indirect treatment approach, the structure is displaced in a direction of ease of motion. Direct treatment approach requires that the structure is displaced in a direction that restricts motion, reaching a restrictive barrier. Additional maneuvers are performed with either technique followed by an assessment phase. During the assessment phase, the structure is then displaced in various directions to ensure improvement of motion.

Physicians in clinical practice subjectively use such palpatory tests of the extremity joints and digits. The difficulty in treating patients with problems of these areas often lies in the inability to make an objective analysis. For example, health care providers who practice manual manipulative medicine claim to have the ability to make musculoskeletal assessment based on factors of quantity and quality. These practitioners are able to palpate the body and formulate treatment based entirely on the diagnosis obtained by palpation. Treatment may include manipulation, physical therapy, medicine, durable medical goods (e.g., ankle brace), surgery or continued observation.

Of particular interest is the assessment of motion quality in terms of tissue response. This is more than a degree of range of motion. Tissue response is how the body reacts to energy transfer. It is the result of a given force supplied, maintained and withdrawn. Terms such as ease of motion and stiffness have been used to describe this dimension of palpatory diagnosis.

Studies have been conducted to define and quantify elasticity, stiffness and motion quantity of the human body. These studies, however, have not been able to correlate the mechanical and clinical concepts of elasticity, stiffness and motion quality.

It would, therefore, be desirable to provide an apparatus and method of use thereof that can provide a quantitative measurement of the myofascial-musculoskeletal elasticity, and, more particularly, to an apparatus and method of use thereof for detecting the elasticity of muscles, ligaments and myofascial structure in the ankle of a patient.

SUMMARY OF THE INVENTION

The invention is an apparatus for detecting myofascial-musculoskeletal elasticity of an ankle of a patient. The apparatus includes means for applying to a foot of a patient a rotational torque in a first direction and in a second, opposite direction, wherein the rotational torque in the first direction is applied in the absence of rotational torque in the second direction, and vice versa, and means for measuring a rotational displacement of the foot in response to the application and removal of the rotational torque in the first and second directions.

The means for applying can include a lever arm having a longitudinal axis positioned transverse, desirably perpendicular, to a longitudinal axis of the foot when said means for applying is coupled to the foot. More particularly, the longitudinal axis of the lever arm is desirably positioned perpendicular to an imaginary line that runs between the center of the heel and the center of the bottom of the forefoot. This imaginary line is also known as the plantar longitudinal axis of the foot.

The rotational torque in the first direction is applied by forcibly moving a first end of the lever arm in the absence of forcible movement of a second end of the lever arm. The rotational torque in the second direction is applied by forcibly moving the second end of the lever arm in the absence of forcible movement of the first end of the lever arm.

The rotational torque applied in the first direction causes rotation about a rotational axis of the foot in a first direction. The rotational torque applied in the second direction causes rotation about the rotational axis of the foot in a second, opposite direction. In practice, in the absence of rotational torque applied in the first and second directions, the rotational axis of the foot is generally located in the corresponding ankle and runs substantially parallel to the plantar longitudinal axis of the foot. As a result of the anatomical structure of the foot and its corresponding ankle, in response to the application of rotational torque in the first and/or second directions, the location and/or orientation of the rotational axis of the foot may change with respect to the plantar longitudinal axis of the foot. More specifically, in response to the increasing application of rotational torque to the foot, the rotational axis of the foot may increasingly move away from a position substantially parallel to the plantar longitudinal axis of the foot. Conversely, in response to the decreasing application of rotational torque, the rotational axis of the foot may return to a position substantially parallel to the plantar longitudinal axis of the foot.

The approximate or general location of the rotational axis of the foot in the corresponding ankle may be determined as follows: while standing with legs and feet pointed forward, roll one foot inwardly against the arch keeping the corresponding leg straight so that weight is applied to the inside of the foot. This is known as rotating the ankle or foot inwardly. Next, roll the foot in the opposite direction placing weight on the outside, small toe, portion of the foot. This is known as rotating the ankle or foot outwardly. The axis about which the foot rotates when rotating the foot inwardly and outwardly is the "rotational axis" of the foot.

The means for applying can further include one or more weights attachable adjacent the first end of the lever arm in the absence of any weight attached to the second end of the lever arm for applying the rotational torque in the first direction and attachable adjacent the second end of the lever arm in the absence of any weight attached to the first end of the lever arm for applying the rotational torque in the second direction.

The rotational torque in the first and second directions are applied transverse, desirably perpendicular, to the plantar longitudinal axis of the foot. The lever arm is desirably positioned adjacent the sole or plantar aspect of the foot.

The means for measuring can include a pointer coupled to the foot, desirably via the lever arm, for rotation therewith and a target for detecting rotation of the pointer during rotation of the foot.

The pointer can be a laser that outputs a beam of light. The target can be a scaled chart or an optical array positioned in the path of the beam of light.

The beam of light can project parallel to the longitudinal axis of the lever arm. The scaled chart or optical array can be positioned perpendicular to the path of the beam of light.

The apparatus can further include a controller coupled to the optical array for recording where the beam of light impinges the optical array.

The apparatus can further include means for positioning the patient so that the muscles associated with a foot and corresponding ankle of the patient are relaxed. The means for positioning can be a seat of sufficient height to permit the lever arm to apply the rotational torque in the first and second directions without contacting a restrictive surface.

The means for applying can further include means for removably coupling the lever arm to the foot. The means for removably coupling can include an assembly configured to support the lever arm and a strap coupled to the assembly. The strap can be configured to removably couple the assembly with the lever arm attached thereto to the sole of the foot. Desirably, when the assembly and the lever arm are coupled to the sole of the foot, the strap crosses over the dorsal structure of the foot and compresses the dorsal structure of the foot and the sole of the foot against the assembly.

The means for applying can include (i) an electric motor; (ii) hydraulic apparatus; and (iii) weights.

The invention is also a method of detecting the elasticity of muscles and associated structures in the foot and corresponding ankle of a patient. The method includes (a) applying to the foot of a patient a first force that causes the foot to rotate inwardly; (b) measuring the rotational displacement of the foot as a function of the applied first force; (c) removing the first force from the foot of the patient; (d) following step (c), measuring the rotational displacement of the foot; (e) applying to the foot of the patient a second force that causes the foot to rotate outwardly; (f) measuring the rotational displacement of the foot as a function of the applied second force; (g) removing the applied second force from the foot of the patient; and (h) following step (g), measuring the rotational displacement of the foot.

The method can further include at least one of: repeating steps (a)-(b) a plurality of cycles, wherein the amount of applied first force is increased in each cycle of step (a); repeating steps (c)-(d) a plurality of cycles, wherein the amount of applied first force is decreased in each cycle of step (c); repeating steps (e)-(f) a plurality of cycles, wherein the amount of applied second force is increased in each cycle of step (e); and repeating steps (g)-(h) a plurality of cycles, wherein the amount of applied second force is decreased in each cycle of step (g).

The method can further include plotting the measured rotational displacements.

The method can further include determining the rotational displacement of the patient's foot inwardly and outwardly as a function of time for each cycle.

Lastly, the method can further include Fourier transforming the rotational displacement of the patient's foot inwardly and outwardly as a function of time for each cycle.

DETAILED DESCRIPTION OF THE INVENTION

The present invention will be described with reference to the accompanying figures where like reference numbers correspond to like elements.

Figure 1:
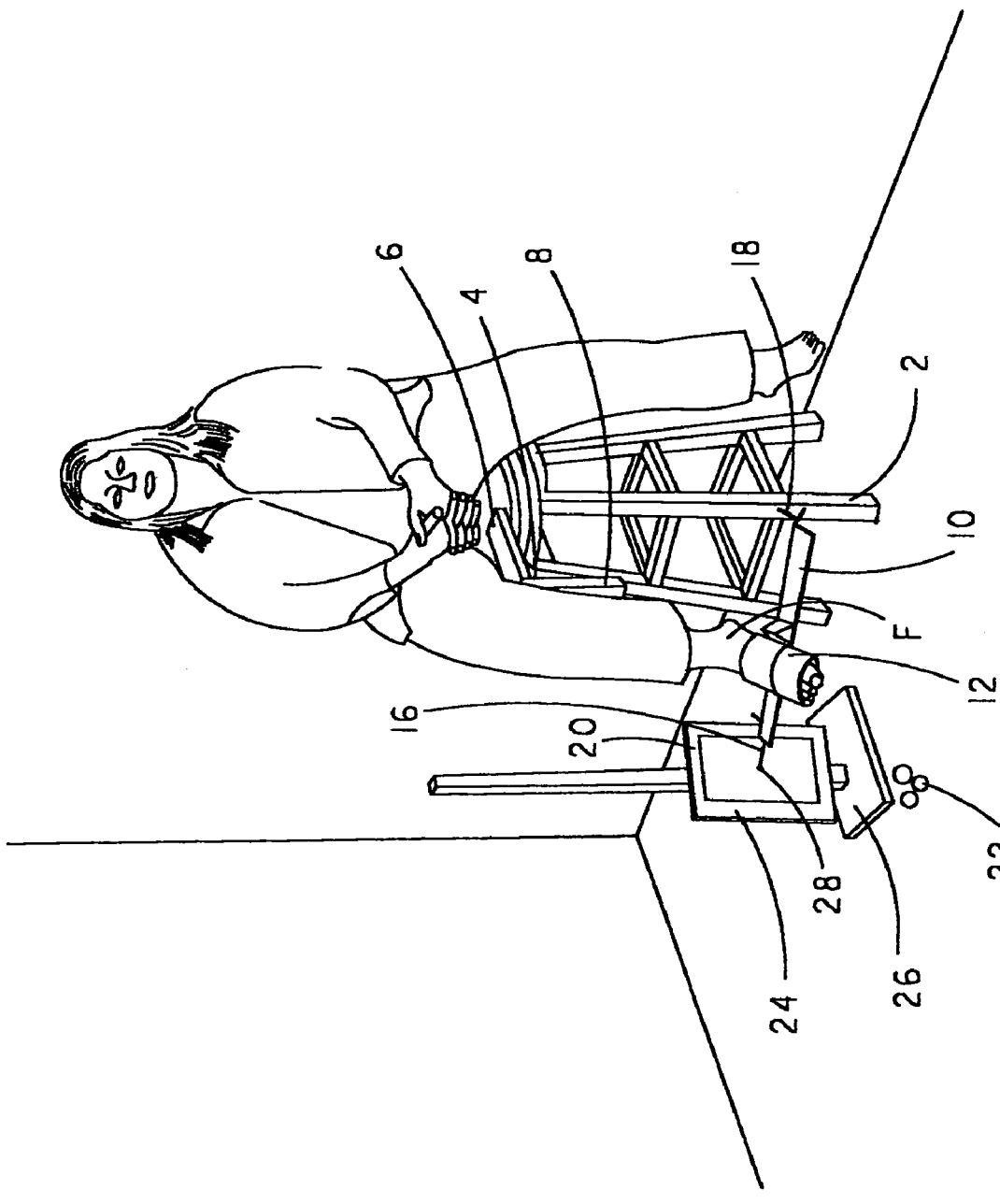
FIG. 1 is a perspective view of an apparatus for detecting ankle torsion coupled to the dangling foot of a seated patient.
Figure 2:
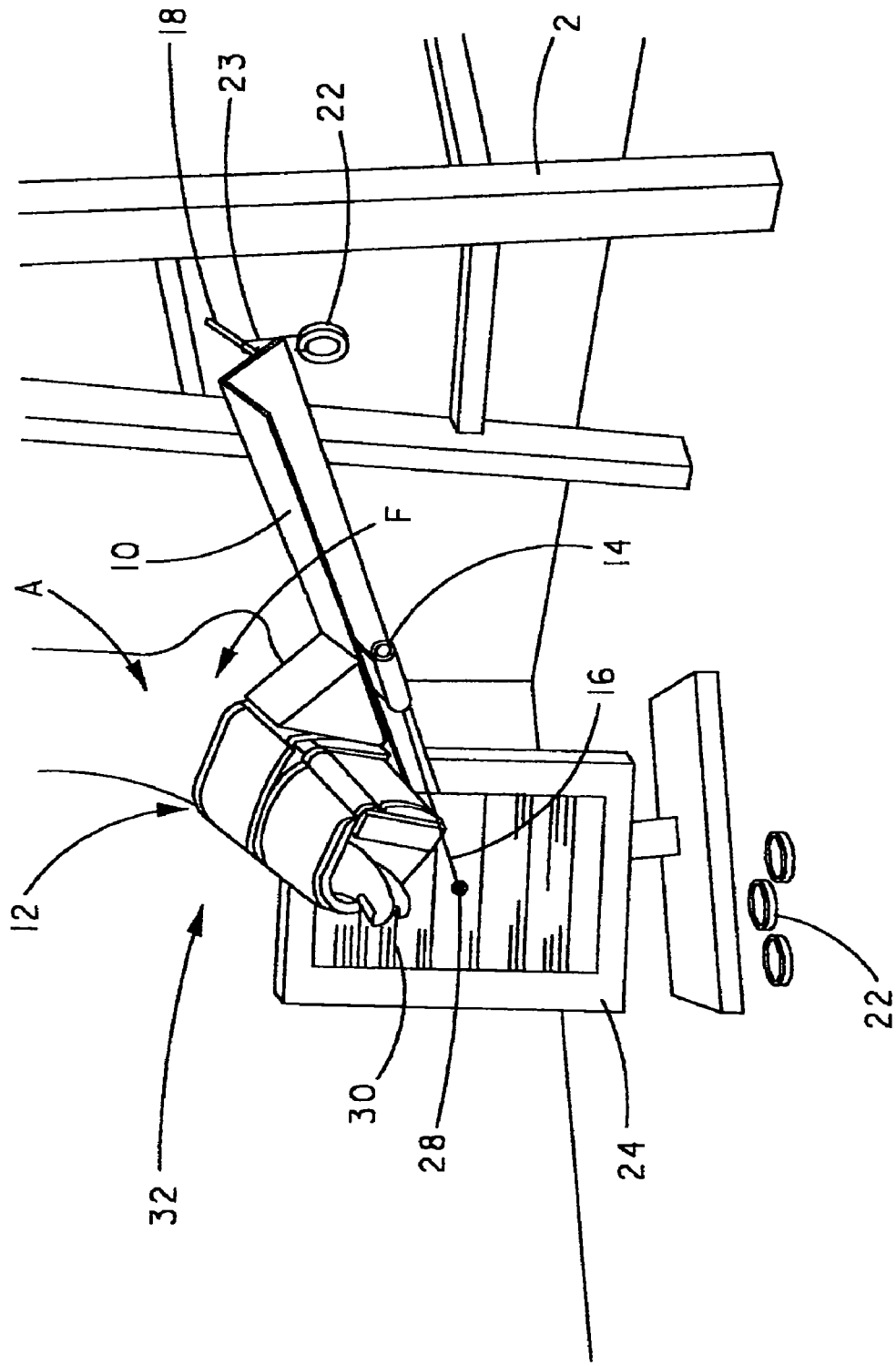
FIGS. 2 and 3 are close-up perspective views of the apparatus attached to the foot of the patient shown in FIG. 1.
Figure 3:
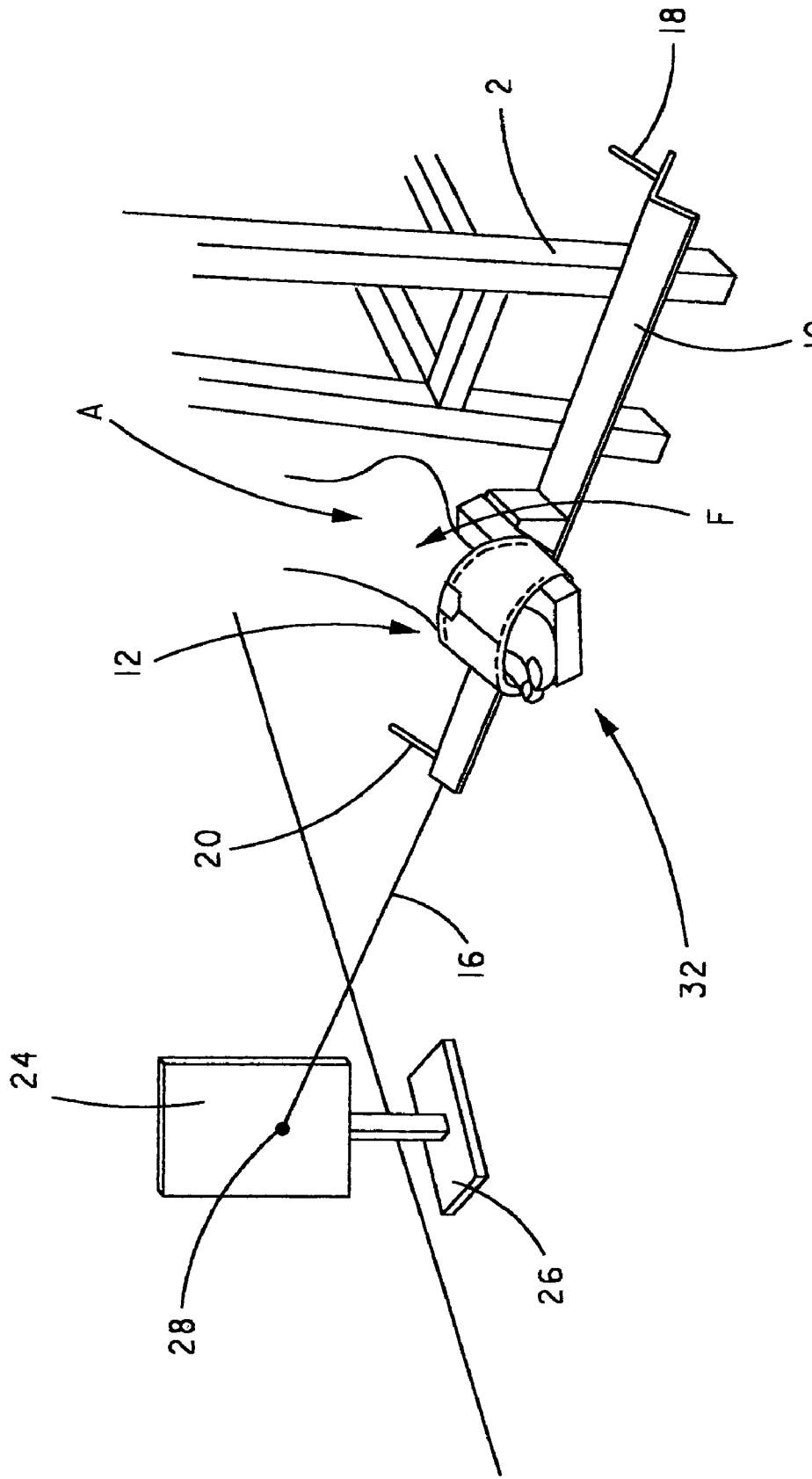

With reference to FIGS. 1-3, one embodiment of an apparatus for detecting ankle torsion includes a seat 2 designed to support a person in a sitting position. Seat 2 can be of any form or variety that permits a patient to assume the sitting position with at least one foot F of the patient dangling or hanging loosely in spaced relation to seat 2. Seat 2 can be of any suitable form including, without limitation, a chair, a table, a stool (as shown in the figures) and the like, that can support the patient in a sitting position with the foot F and ankle A of the patient under examination dangling freely. For purpose of describing the invention, the figures illustrate seat 2 as being a stool. However, this is not to be construed as limiting the invention.

Optionally, seat 2 may include a leg guide 4 configured to facilitate dangling of the patient's foot while the patient is in the sitting position on seat 2. The embodiment of leg guide 4 shown in FIG. 3 includes a horizontal surface 6 for supporting the backside of the patient's upper leg when the patient is sitting on seat 2 and a vertical surface 8 against which the backside or calf side of the patient's lower leg rests against during torsional testing of the ankle A under examination.

A lever arm 10 is removably coupled to the patient's suspended or dangling foot F. When attached to the patient's foot F, lever arm 10 is positioned laterally, desirably perpendicular, to a longitudinal axis of the foot adjacent the sole of the foot. More particularly, a longitudinal axis of lever arm 10 is positioned laterally, desirably perpendicular, to a plantar longitudinal axis (not shown) of the patient's foot F that extends between the center of the heel and the center of the bottom of the forefoot. Desirably, lever arm 10 is positioned below the sole or arch of the patient's foot, with the patient's foot positioned intermediate the ends of lever arm 10.

Lever arm 10 can be attached to the patient's foot by any suitable attachment means, such as the illustrated block and strap(s) assembly 12. The illustration of block and strap(s) assembly 12, however, is not to be construed as limiting the invention.

A directional light source, such as a laser 14, is attached to lever arm 10. Desirably, laser 14 is attached to lever arm 10 on a side thereof opposite the sole of the patient's foot. However, this is not to be construed as limiting the invention.

In the illustrated embodiment, laser 14 is attached to lever arm 10 such that a beam of light 16 output by laser 14 extends substantially parallel to the longitudinal axis of lever arm 10. However, this is not to be construed as limiting the invention since it is envisioned that laser 14 can be positioned on lever arm 10 with beam of light 16 extending in a suitable direction to facilitate measurement of the patient's ankle in the manner to be described hereinafter.

Lever arm 10 includes a medial weight carrier 18 and a lateral weight carrier 20 positioned on or adjacent opposite ends of lever arm 10. When lever arm 10 is attached to the patient's foot in the manner shown in the figures, medial weight carrier 18 is positioned on the medial, or big toe, side of the foot while lateral weight carrier 20 is positioned on the lateral, or little toe, side of the foot.

Each weight carrier 18 and 20 is configured to support one or more weights 22 that can be removably attached thereto during torsional testing of the patient's ankle. The illustration of each weight carrier 18 and 20 being an elongated member to which each weight 22 can be connected by way of a hook 23 is not to be construed as limiting the invention since it is envisioned that any suitable means can be utilized for removably attaching one or more weights 22 on or adjacent the ends of lever arm 10.

In use of lever arm 10 to measure the myofascial-musculoskeletal elasticity of the patient's ankle, a target 24 is positioned substantially perpendicular to and in the path of light beam 16. In the illustrated embodiment, target 24 is supported by a target stand 26. However, this is not to be construed as limiting the invention since target 24 can be supported substantially perpendicular to the path of light beam 16 in any suitable manner, e.g., a wall.

The interaction of light beam 16 on target 24 produces a laser spot 28 thereon. Desirably, target 24 is positioned a fixed, desirably predetermined, distance from an axis of rotation of the foot, which also is the axis of rotation of lever arm 10. The axis of rotation of the foot does not necessarily lie directly above the plantar longitudinal axis of the foot. The approximate location of the axis of rotation of the foot can be determined as follows: while standing with legs and feet pointed forward, roll one foot inwardly against the arch keeping the leg straight so that weight is applied to the inside, big toe portion of the foot. This is known as rotating the ankle or foot inwardly. Next, roll the foot in the opposite direction placing weight on the outside, small toe, portion of the foot. This is known as rotating the foot outwardly. The axis about which the foot rotates in response to rotating the foot inwardly and outwardly is generally considered by those skilled in the art to be the axis of rotation of the foot.

Target 24 can include a plurality of spaced parallel lines 30 that are spaced from each other a predetermined distance. The predetermined distance between each pair of lines is selected so that for x degrees of rotation of the patient's ankle clockwise or counterclockwise, laser spot 28 moves a predetermined number of lines 30.

Alternatively, target 24 can include a calibrated grid having a plurality of spaced parallel horizontal lines and a plurality of intersecting, spaced parallel vertical lines. The spacing between each pair of adjacent horizontal lines and the spacing between each pair of adjacent spaced vertical lines can be selected in any suitable manner.

The combination of lever arm 10, weight carriers 18 and 20, and block and strap(s) assembly 12 comprise a so-called ankle unit 32. Because the feet of a patient are axisymmetrical with respect to the medial axis of the patient, it is envisioned that an ankle unit designed specifically for the right foot of a patient will be used therewith and an ankle unit designed for use on the left foot of the patient will be used exclusively therewith. However, this is not to be construed as limiting the invention since it is envisioned that a single ankle unit can be configured for use with both feet of the patient.

The use of ankle unit 32 with laser 14 attached thereto in the manner described above will now be described.

Initially, the patient is seated on seat 2 with the backside of her upper leg desirably supported by a suitable means, such as leg guide 4, and with the foot F of said leg hanging suspended therefrom. Ankle unit 32 with laser 14 attached thereto in the manner described above is attached to the patient's suspended foot F such that lever arm 10 is positioned beneath the sole of the patient's foot with laser 14 pointing in a suitable direction to produce laser spot 28 on target 24 positioned a suitable distance from the axis of rotation of the foot F. Desirably, the materials forming ankle unit as well as laser 14 are selected such that the weight thereof minimize extension of the patient's ankle, but allow rotation about the axis of rotation of the foot F. If necessary, the vertical height of target 24 can be adjusted such that during rotational testing of the patient's ankle, in both the clockwise and counterclockwise directions, laser spot 28 remains on target 24.

Next, starting with the patient's foot F in an initial, starting position, the initial position of laser spot 28 on target 24 is recorded in the absence of any weight 22 attached to medial weight carrier 18 or lateral weight carrier 20. Then, weight 22 is attached to medial weight carrier 18, whereupon the patient's foot rotates inwardly and the new location of laser spot 28 on target 24 is recorded. Thereafter, the process of incrementally adding weight 22 to medial weight carrier 18 and recording the new location of laser spot 28 on target 24 after each incremental addition of weight 22 continues until a maximum desired weight 22 has been added to medial weight carrier 18. In an exemplary embodiment, a maximum of three (3) two ounce weights 22 are added to medial weight carrier 18. However, this is not to be construed as limiting the invention.

Once the maximum desired amount of weight has been added to medial weight carrier 18, weight 22 is incrementally removed from medial weight carrier 18 whereupon the patient's foot rotates back toward the starting position. After each incremental removal of weight 22 from medial weight carrier 18, the new location of laser spot 28 on target 24 is recorded. The process of incrementally removing weight 22 from medial weight carrier 18 and recording the new location of laser spot 28 on target 24 after each incremental removal of weight 22 continues until no weight 22 is attached to medial weight carrier 18.

Next, a weight 22 is attached to lateral weight carrier 20, whereupon the patient's foot rotates outwardly and the new position of laser spot 28 on target 24 is recorded. Thereafter, the process of incrementally adding weight 22 to lateral weight carrier 20 and recording the new location of laser spot 28 on target 24 after each incremental addition of weight 22 continues until a maximum desired weight 22 has been added to lateral weight carrier 20.

Thereafter, the weight 22 attached to lateral weight carrier 20 is incrementally removed, whereupon the patient's foot rotates back toward the starting position, and the new location of laser spot 28 on target 24 is recorded after each incremental removal of weight 22 from lateral weight carrier 20 until no weight 22 is attached to lateral weight carrier 20. In an exemplary embodiment, a maximum of three (3) two ounce weights are added to lateral weight carrier 20. However, this is not to be construed as limiting the invention.

The foregoing process of incrementally adding and incrementally removing weight 22 to and from medial weight carrier 18 and lateral weight carrier 20, and the recording of the position of laser spot 28 on target 24 after each incremental addition and removal, can continue for a desired number of cycles. Thereafter, ankle unit 32 and laser 14 can be removed from the foot of the patient. If desired, the foregoing procedure can be repeated on the patient's other foot.

Figure 4:
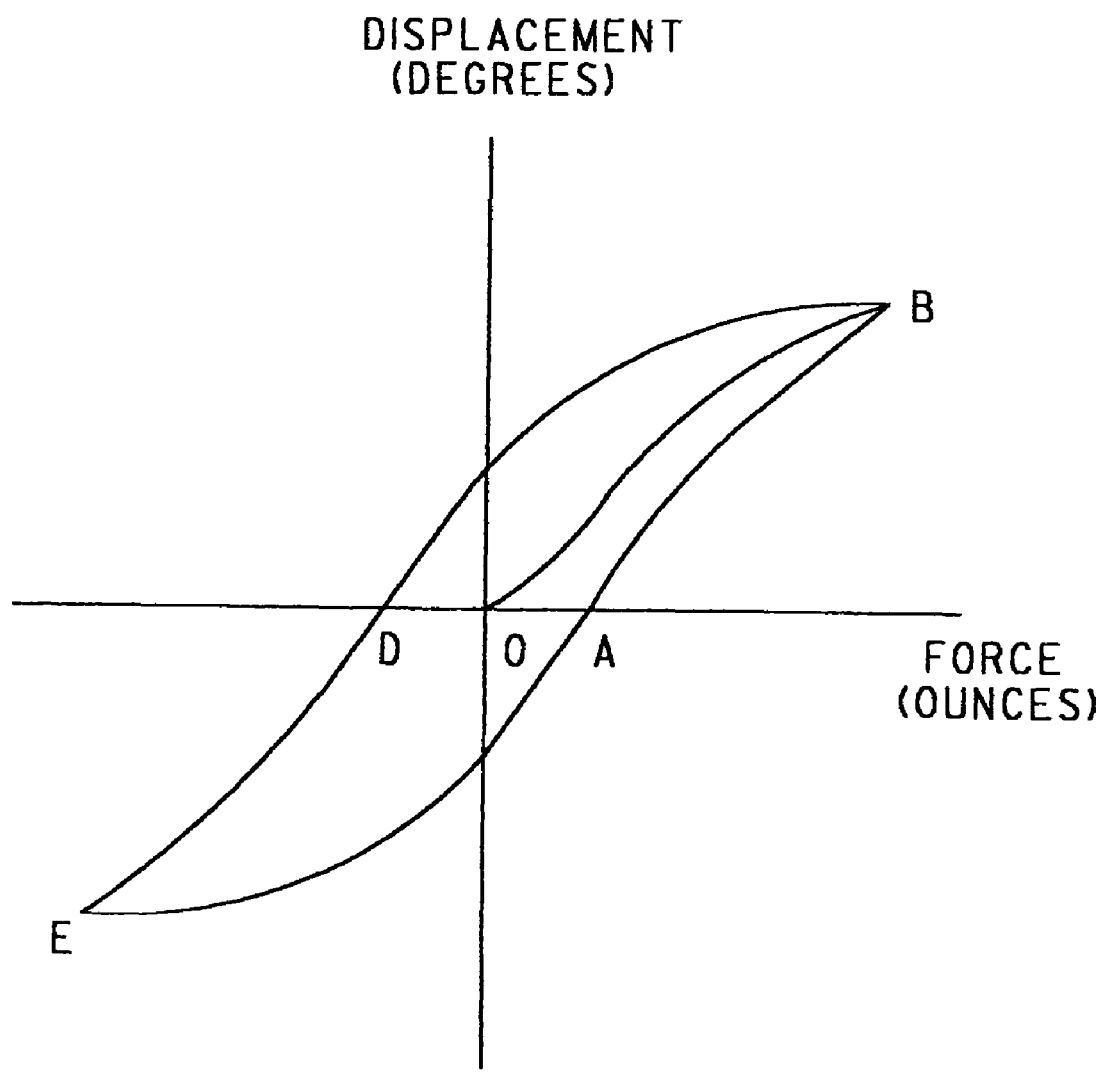
FIG. 4 is an ideal displacement versus force hysteresis curve produced from data acquired utilizing the apparatus shown in FIGS. 1-3.
Figure 5:
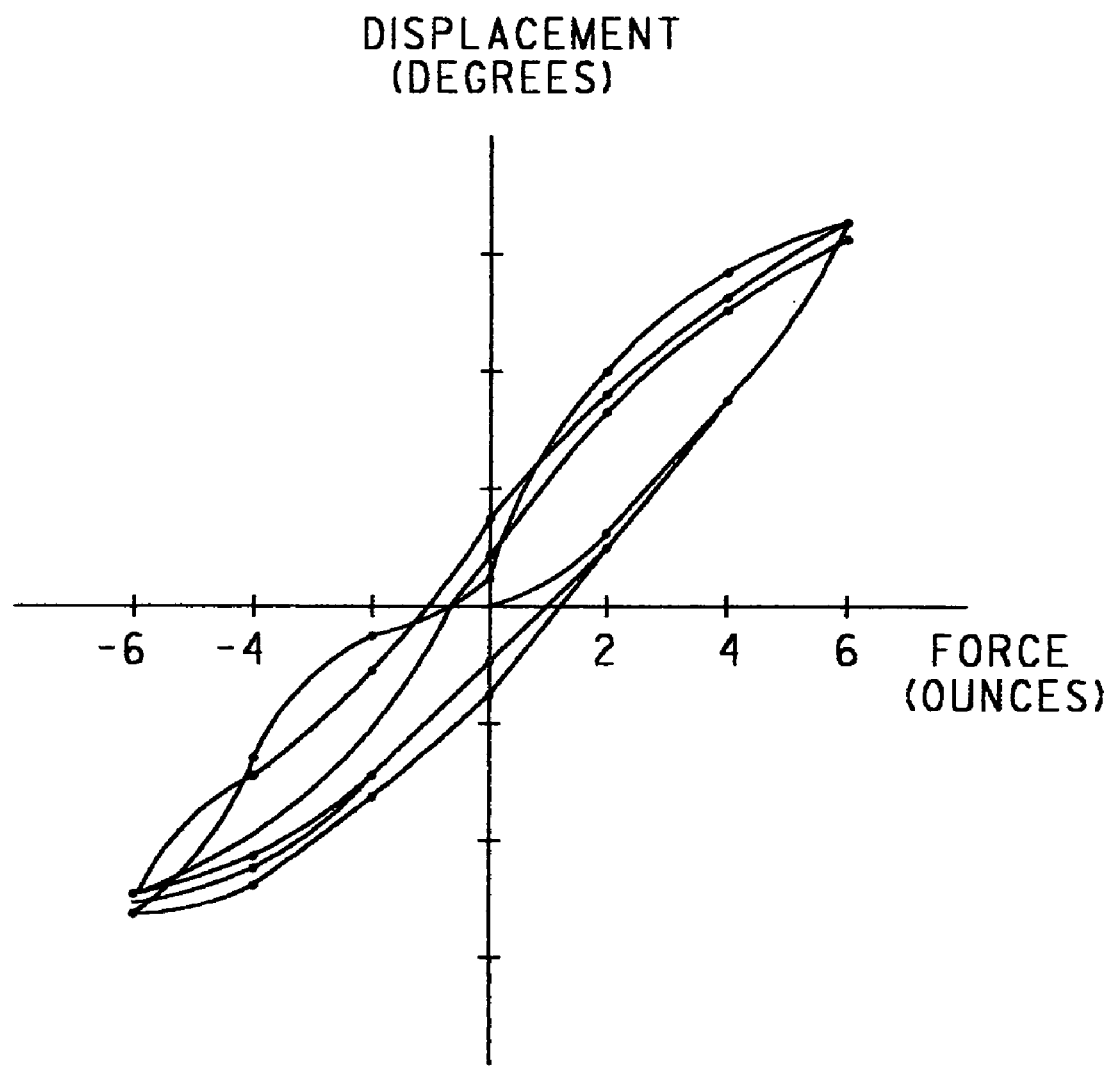
FIG. 5 is a number of displacement versus force hysteresis curves produced from data acquired by the apparatus shown in FIGS. 1-3 when used on a normal ankle.

With reference to FIGS. 4 and 5 and with continuing reference to FIGS. 1-3, next, the recorded positions of laser spot 28 on target 24 as a function of the corresponding force, e.g., the amount of weight, applied to medial weight carrier 18 and lateral weight carrier 20 are plotted as points on a Cartesian coordinate system. Once the plot of the recorded positions of laser spot 28 on target 24 versus force is complete, a continuous line is drawn connecting adjacent points to form the hysteresis curve shown in FIG. 5.

FIG. 4 illustrates an ideal displacement versus force hysteresis curve. In the hysteresis curve shown in FIG. 4, the path between points O and B is the displacement versus force path taken in response to the initial addition of maximum weight 22 to medial weight carrier 18. The path between points B and D is the displacement versus force path taken in response to the removal of all weight 22 from medial weight carrier 18. The path between points D and E is the displacement versus force path taken in response to the initial addition of maximum weight 22 to lateral weight carrier 20. The path between points E and A is the displacement versus force path taken in response to the removal of all weight 22 from lateral weight carrier 20. Lastly, the path between points A and B is the displacement versus force path taken in response to the reintroduction of maximum weight 22 to medial weight carrier 18 during the next test cycle.

As can be seen in FIG. 5, except for the initial attachment of maximum weight 22 to medial weight carrier 18, corresponding to the path between points O and B in FIG. 4, each cycle of loading weight on and off of medial and lateral weight carriers 18 and 20 produces a hysteresis curve. Moreover, the hysteresis curve produced for each cycle of loading weight on and off of medial and lateral weight carriers 18 and 20 are generally the same.

Figure 6:
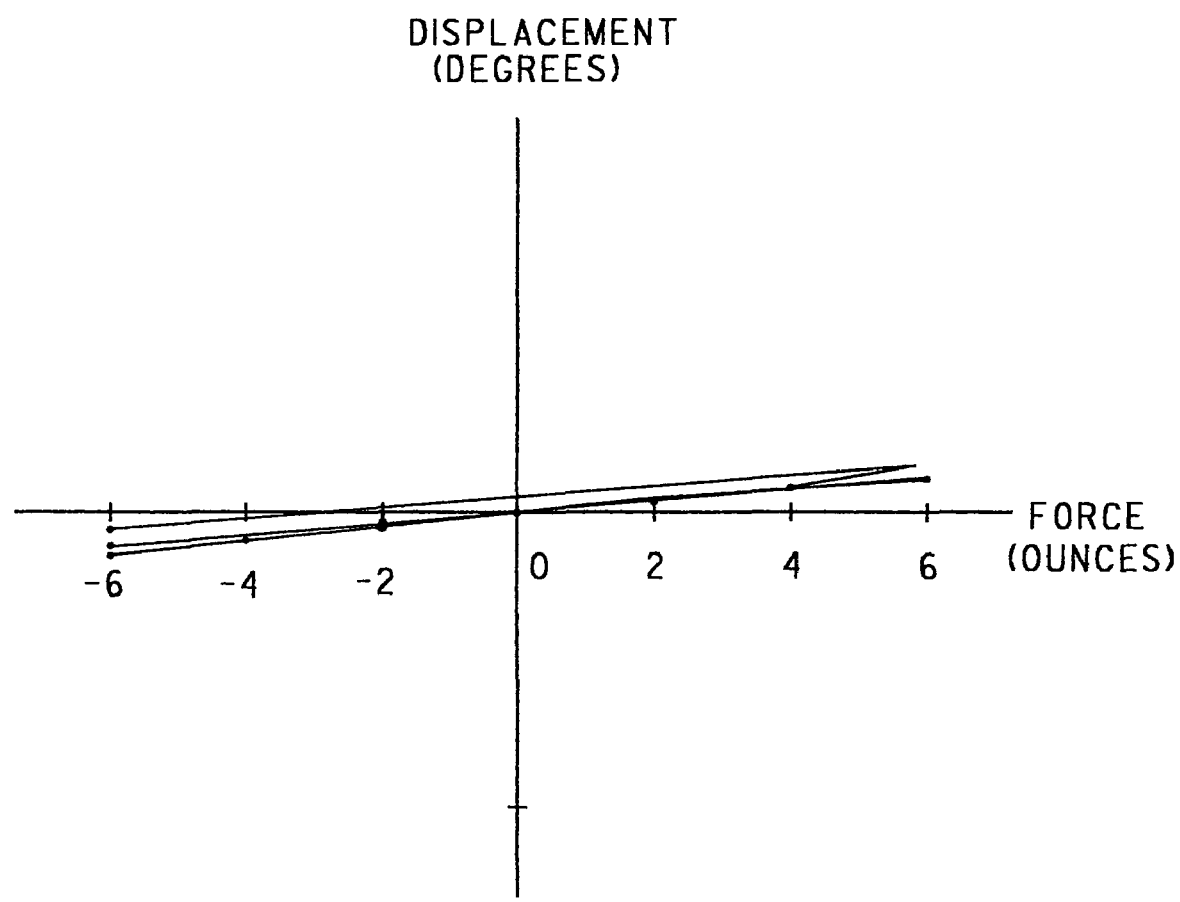
FIG. 6 is a displacement versus force hysteresis curve produced utilizing the apparatus shown in FIGS. 1-3 when used on an ankle whose rotation was artificially constrained.

The exemplary hysteresis curve shown in FIG. 4 and the actual hysteresis curve shown in FIG. 5 are representative of a normal ankle. In contrast, the displacement versus force hysteresis curve shown in FIG. 6 was obtained in the above-described manner from an ankle whose rotation was artificially constrained. It is believed that an ankle that is injured or diseased will have a hysteresis curve like the hysteresis curve shown in FIG. 6.

Figure 7:
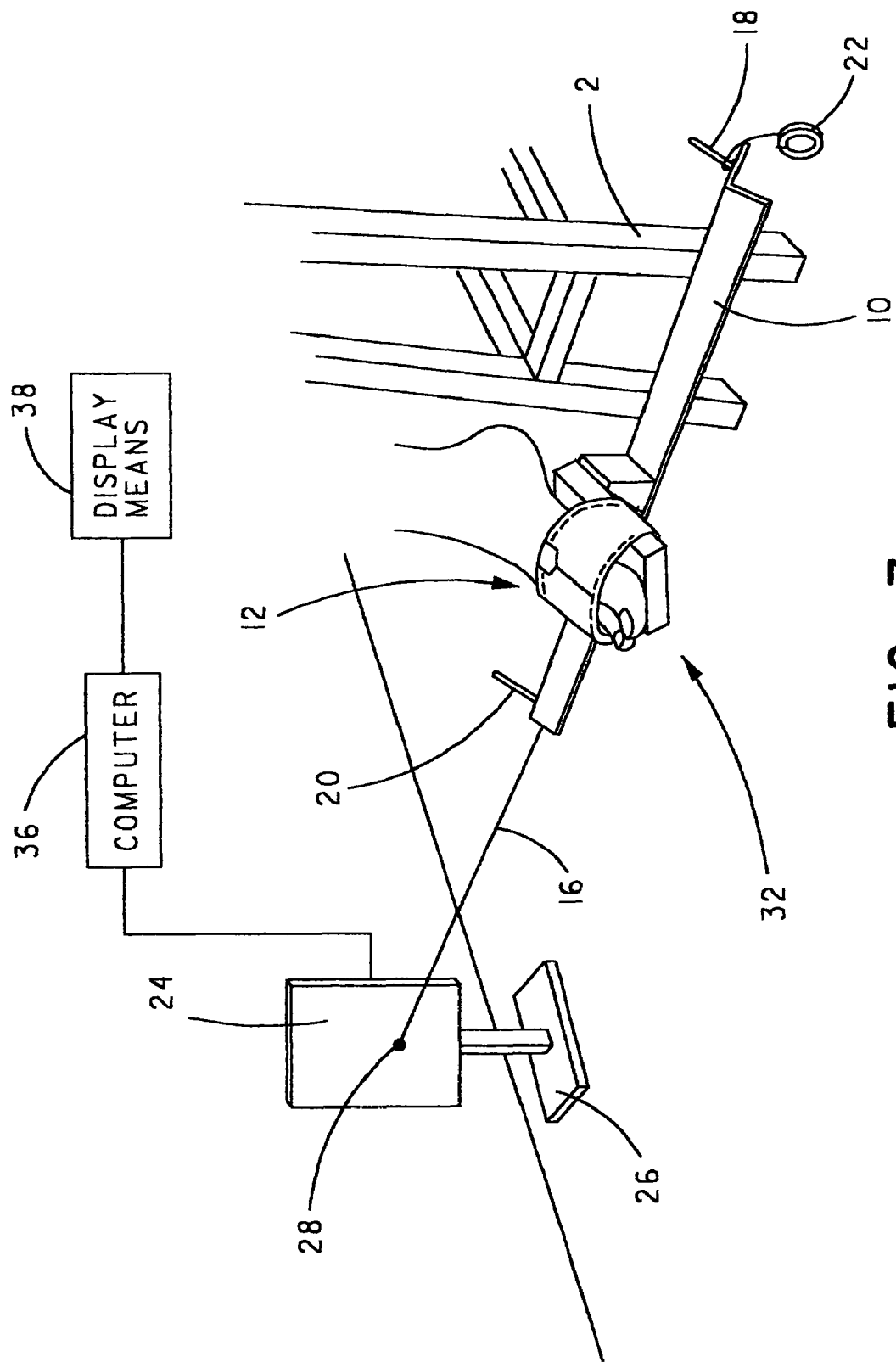
FIG. 7 is a perspective view of another embodiment of an apparatus for detecting foot and ankle torsion in accordance with the present invention.

With reference to FIG. 7 and with reference back to FIGS. 1-3, in the embodiment shown in FIGS. 1-3, target 24 is illustrated as being a sheet of suitable material, e.g., paper, Mylar, and the like. If desired, however, target 24 can be an optical array for detecting the position of laser spot 28 thereon. Target 24 in the form of an optical array can be coupled to a computer 36 which can be operative for recording the position of laser spot 28 on target 24. After recording the starting position of laser spot 28 on target 24 and recording the position of laser spot on target 24 after each incremental addition and each incremental removal of weight to weight carriers 18 and 20 in the manner described above for the desired number of cycles, computer 36 can cause one or more displacement versus force hysteresis curves to be displayed on a suitable display means 38, such as a printer or a visual display, such as a CRT, an LCD display, a plasma display, a projection display, and the like. Since it is envisioned that any suitable display means 38 can be utilized for displaying the hysteresis curve(s) generated by computer 36, the foregoing recitation of various display means is not to be construed as limiting the invention.

Figure 8:
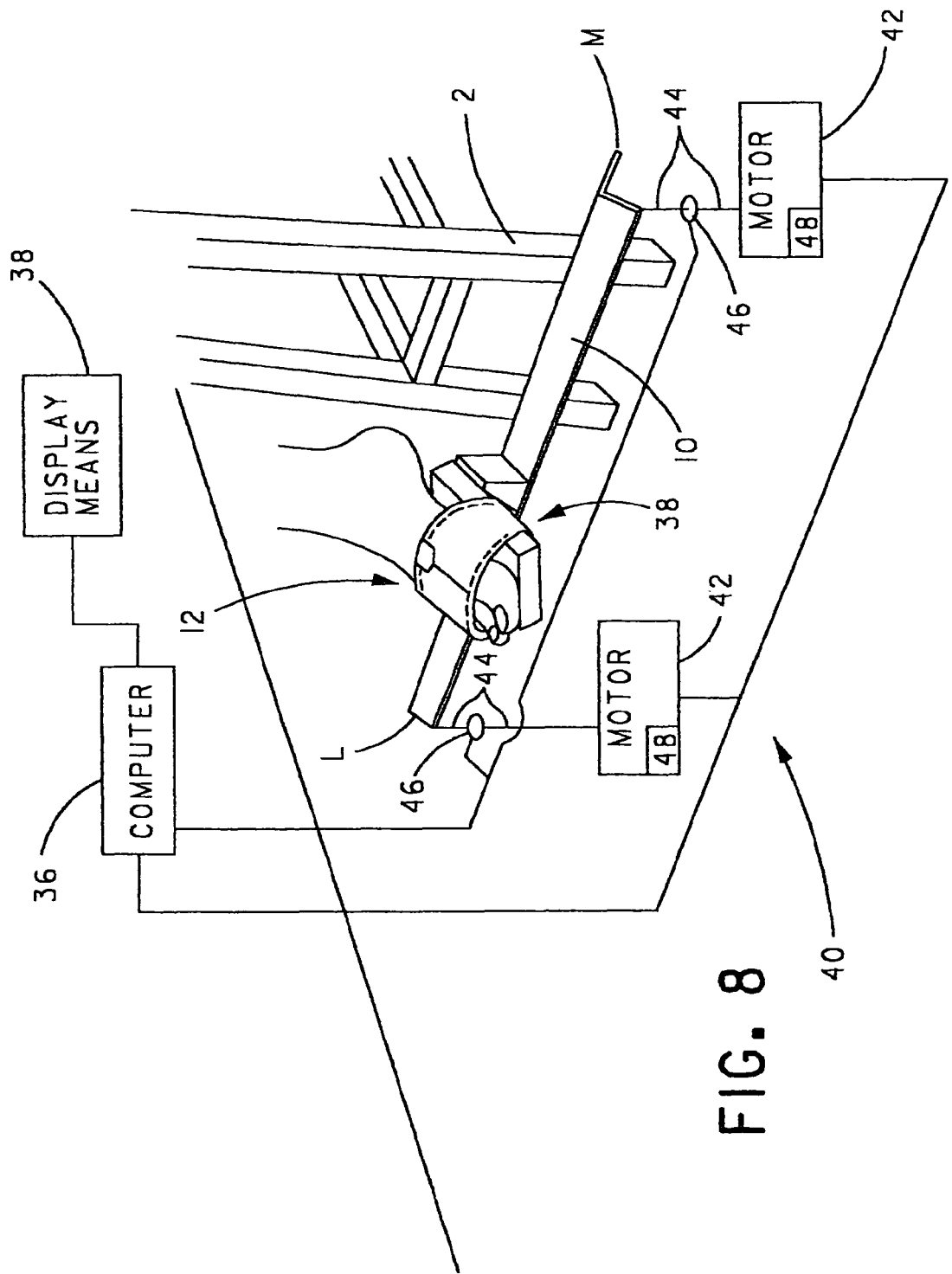
FIG. 8 is a perspective view of another embodiment of an apparatus for detecting foot and ankle torsion in accordance with the present invention.

With reference to FIG. 8, in the embodiment shown in FIGS. 1-3, weight carriers 18 and 20 and weights 22 were utilized as a means for applying force to the ends of lever arm 10. Alternatively, one or both of weight carriers 18 and 20 and weights 22 can be omitted and replaced by a suitable electromechanical or hydraulic force applying means 40 for applying force to the ends of lever arm 10.

For example, force applying means 40 can include one or more electric motors 42 coupled to one or both ends of lever arm 10 and operating under the control of computer 36. Each motor 42 can be coupled to the corresponding end of lever arm 10 via a cord or line 44. A force measuring means 46, such as a load cell or torque sensor, can be provided with each motor 42 for measuring a force applied to an end of lever arm 10 by the corresponding motor 42 and line 44. Force measuring means 46 is desirably coupled to computer 36 for transferring to computer 36 an electric signal related to the force measured thereby. Lastly, each motor 42 desirably includes a displacement measuring means 48, such as an encoder or resolver, which is coupled to computer 36 for reporting to a computer 36 a displacement corresponding to the displacement of the corresponding end of lever arm 10 in response to the application of force thereon by said electric motor 42.

In operation, beginning from a starting position where no force is applied to lever arm 10 by any motor 42, under the control of computer 36 and force measuring means 46, the motor 42 coupled to the medial end M of lever arm 10 is controlled to incrementally increase the amount of downward directed force applied to the medial end M of lever arm 10. At the same time, the motor 42 coupled to the lateral end L of lever arm 10 is controlled so as to not apply any downward force thereto. Utilizing the appropriate measuring means 48 associated with the motor 42 coupled to the medial end M of lever arm 10, computer 36 records the displacement of the medial end M of lever arm 10 from a starting position in response to each incremental addition of force applied to the medial end M of lever arm 10 by said motor 42. Thus, the combination of electric motor 42, line 44, force measuring means 46 and displacement measuring means 48 associated with each end of lever arm 10 along with computer 36 can replace weight carriers 18 and 20, weights 22, laser 14 and target 24 in the embodiment illustrated in FIGS. 1-3.

Upon application of the maximum desired downward force to the medial end M of lever arm 10 by the motor 42 coupled thereto, computer 36 causes said motor 42 to incrementally reduce the force applied thereto. For each incremental reduction in said force, computer 36 measures the displacement of the medial end M lever arm 10 from the starting position via the corresponding displacement measuring means 48. The process of incrementally reducing the force applied to the medial end M of lever arm 10 and the recording of the displacement of lever arm 10 from the starting position continues until no further force is applied to the medial end M of lever arm 10 by the corresponding motor 42.

Thereafter, the foregoing process of incrementally adding force to the lateral end L of lever arm 10, incrementally decreasing the force applied to the lateral end L of lever arm 10 and recording of the displacement of lever arm 10 from the starting position in response to each incremental addition or reduction of force is repeated under the control of computer 36 via the electric motor 42, the line 44, the force measuring means 46 and the displacement measuring means 48 associated with the lateral end L of lever arm 10.

The process of applying and removing force to the medial and lateral ends of lever arm 10 can be repeated for any number of cycles until a desired number of force versus displacement data points have been acquired. Thereafter, computer 36 can display on display means 38 one or more hysteresis curves of the type shown in FIG. 5 from these data points.

As can be seen, the use of computer 36 along with each electric motor 42, each line 44, each force measuring means 46 and each displacement measuring means 48 can be substituted for weight carriers 18 and 20, weights 22, laser 14 and target 24.

In an alternate embodiment, a suitable hydraulic apparatus (not shown) can be utilized as the force applying means 40 in place of one or both electric motors 42.

The foregoing embodiments of an apparatus for applying rotational torque to the ankle of a patient are not to be construed as limiting the invention since it is envisioned that any other suitable means for applying a controlled rotational torque, in both the clockwise and counterclockwise directions, to the ankle of the patient and for measuring rotational displacement of the ankle in response to the application and removal of said force can be utilized.

If desired, the rotational displacement of the patient's ankle in both directions can be determined as a function of time for each cycle to provide additional diagnostic information regarding the health of the patient's ankle. Moreover, if desired, a Fourier transform of the rotational displacement of the patient's ankle in both directions as a function of time can also be determined for each cycle to provide even further diagnostic information regarding the health of the patient's ankle.

As can be seen, the present invention enables quantitative assessment of the elasticity of muscles, ligaments and myofascial structure in the foot and ankle of a patient. It also provides a means for determining a change in the elasticity of the muscles, ligaments myofascial structure in the foot and ankle of the patient over time by comparing hysteresis plots of the same foot and ankle taken over said period of time.

The invention has been described with reference to the preferred embodiments. Obvious modifications and alterations will occur to others upon reading and understanding the preceding detailed description. For example, in the embodiment shown in FIGS. 1-3, laser 14 and target 24 can be replaced by any other suitable means attached to lever arm 10 for detecting and providing a user discernable indication of rotational displacement thus avoiding the need for laser 14 and target 24. Exemplary, non-limiting examples of such means include: the CXTLA01 or CXTLA02 solid-state tilt sensor available from Crossbow Technology, Inc. of San Jose, Calif.; the SQ-SI-360DA solid-state MEMS inclinometer available from Signal Quest, Inc of Lebanon, N.H.; a ball and/or bubble level or inclinometer of the type available from Level Developments Ltd, of Croydon, Surrey, United Kingdom; any of the types of electronic inclinometers available from Level Developments Ltd, of Croydon, Surrey, United Kingdom; and the like. It is intended that the invention be construed as including all such modifications and alterations insofar as they come within the scope of the appended claims or the equivalents thereof.

The invention claimed is:

1. An apparatus for detecting myofascial-musculoskeletal elasticity of an ankle of a patient, said apparatus comprising:
   means for applying to a foot of a patient when the foot is dangling a rotational torque in a first direction and in a second, opposite direction, wherein the rotational torque in the first direction is applied in the absence of rotational torque in the second direction, and vice versa; and
   means for measuring displacement of the corresponding ankle in response to the application and removal of the rotational torque in the first and second directions.

2. The apparatus of claim 1, wherein said means for applying includes a lever arm having a longitudinal axis positioned transverse to a longitudinal axis of the foot when said means for applying is coupled to the foot.

3. The apparatus of claim 2, wherein:
   the rotational torque in the first direction is applied by forcibly moving a first end of the lever arm in the absence of forcible movement of a second end of the lever arm; and
   the rotational torque in the second direction is applied by forcibly moving the second end of the lever arm in the absence of forcible movement of the first end of the lever arm.

4. The apparatus of claim 3, wherein:
   the rotational torque applied in the first direction causes rotation of the foot one of inwardly and outwardly; and
   the rotational torque applied in the second direction causes rotation of the foot the other of inwardly and outwardly.

5. The apparatus of claim 4, wherein the means for applying further includes one or more weights attachable adjacent the first end of the lever arm in the absence of any weight attached to the second end of the lever arm for applying the rotational torque in the first direction and attachable adjacent the second end of the lever arm in the absence of any weight attached to the first end of the lever arm for applying the rotational torque in the second direction.

6. The apparatus of claim 1, wherein the rotational torque in the first and second directions is applied transverse to a rotational axis of the foot.

7. The apparatus of claim 2, wherein the lever arm is positioned adjacent the sole of the foot.

8. The apparatus of claim 2, wherein the means for measuring includes:
   a pointer coupled to the foot for rotation therewith; and
   a target for detecting rotation of the pointer in response to the displacement of the foot.

9. The apparatus of claim 8, wherein the pointer is coupled to the lever arm.

10. The apparatus of claim 8, wherein:
    the pointer is a laser that outputs a beam of light; and
    the target is one of a scaled chart and an optical array positioned in the path of the beam of light.

11. The apparatus of claim 10, wherein the beam of light projects parallel to the longitudinal axis of the lever arm.

12. The apparatus of claim 10, wherein the scaled chart or optical array is positioned perpendicular to the path of the beam of light.

13. The apparatus of claim 10, further including a controller coupled to the optical array for recording where the beam of light impinges on the optical array.

14. The apparatus of claim 1, further including means for positioning the patient so that the muscles associated with a foot and corresponding ankle of the patient are relaxed.

15. The apparatus of claim 1, wherein the means for positioning is a seat of sufficient height to permit the lever arm to apply rotational torque in the first and second directions without contacting a restrictive surface.

16. The apparatus of claim 1, wherein the means for applying further includes means for removable coupling the lever arm to the foot.

17. The apparatus of claim 16, wherein the means for removably coupling includes:
   an assembly configured to support the lever arm; and
   a strap coupled to the assembly, the strap configured to removably couple the assembly with the lever arm attached thereto to the sole of the foot.

18. The apparatus of claim 1, wherein the means for applying includes one of the following:
   (i) an electric motor;
   (ii) hydraulic apparatus; or
   (iii) weights.

19. A method of detecting the elasticity of muscles and associated structures in a foot and corresponding ankle of a patient, the method comprising:
   (a) applying to the foot of a patient when the foot is dangling a first force that causes the foot to rotate inwardly;
   (b) measuring the displacement of the foot as a function of the applied first force;
   (c) removing the first force from the foot of the patient;
   (d) following step (c), measuring the displacement of the foot;
   (e) applying to the foot of the patient a second force that causes the foot to rotate outwardly;
   (f) measuring the displacement of the foot as a function of the applied second force;
   (g) removing the second force from the foot of the patient; and
   (h) following step (g), measuring the displacement of the foot.

20. The method of claim 19, further including:
   repeating steps (a)-(b) a plurality of cycles, wherein the amount of the applied first force is increased in each cycle of step (a);
   repeating steps (c)-(d) a plurality of cycles, wherein the amount of the applied first force is decreased in each cycle of step (c);
   repeating steps (e)-(f) a plurality of cycles, wherein the amount of the applied second force is increased in each cycle of step (e); and
   repeating steps (g)-(h) a plurality of cycles, wherein the amount of the applied second force is decreased in each cycle of step (g).

21. The method of claim 19, further including plotting the measured displacements.

22. The method of claim 19, further including repeating steps (a)-(h) a plurality of cycles.

23. The method of claim 22, further including determining the displacement of the foot inwardly and outwardly as a function of time for each cycle.

24. The method of claim 22, further including Fourier transforming the rotational displacement of the patient's foot inwardly and outwardly as a function of time for each cycle.

* * * * *